(12) United States Patent
Cooney, III et al.

(10) Patent No.: US 9,655,726 B2
(45) Date of Patent: May 23, 2017

(54) RADIAL-CAPITELLAR IMPLANT

(75) Inventors: William P. Cooney, III, Rochester, MN (US); Bernard F. Morrey, Rochester, MN (US); David A. Leibel, Princeton, MN (US)

(73) Assignee: Mayo Foundation for Medical Research and Education, Rochester, MN (US)

( * ) Notice: Subject to any disclaimer, the term of this patent is extended or adjusted under 35 U.S.C. 154(b) by 2257 days.

(21) Appl. No.: 11/605,808

(22) Filed: Nov. 28, 2006

(65) Prior Publication Data

US 2007/0073409 A1    Mar. 29, 2007

Related U.S. Application Data

(63) Continuation of application No. 11/001,662, filed on Dec. 1, 2004, now Pat. No. 7,160,329.

(51) Int. Cl.
*A61F 2/38*        (2006.01)
*A61F 2/30*        (2006.01)

(52) U.S. Cl.
CPC ........ *A61F 2/3804* (2013.01); *A61F 2/30767* (2013.01); *A61F 2002/30153* (2013.01); *A61F 2002/30332* (2013.01); *A61F 2002/30354* (2013.01); *A61F 2002/30574* (2013.01); *A61F 2002/30604* (2013.01);
(Continued)

(58) Field of Classification Search
CPC .. A61F 2002/30665; A61F 2002/30663; A61F 2002/3827; A61F 2002/3809; A61F 2/3804; A61F 2002/3686; A61F 2002/30176; A61F 2002/30161; A61F 2002/30894; A61F 2002/30611; A61F 2002/30479; A61F 2002/30378; A61F 2002/3822; A61F 2/3854; A61F 2/38;
(Continued)

(56) References Cited

U.S. PATENT DOCUMENTS 3,651,521 A    3/1972  Devas
3,707,006 A    12/1972  Bokros et al.
(Continued)

FOREIGN PATENT DOCUMENTS

DE    4331282 A1    3/1995
GB    1567007 A     5/1980
(Continued)

OTHER PUBLICATIONS

BIOMET, Liverpool™ Radial Head Replacement, website printout located at www.biomet.com/products/index.cfm?p=090005, unknown date.
(Continued)

*Primary Examiner* — Christian Sevilla
*Assistant Examiner* — Cheryl Miller
(74) *Attorney, Agent, or Firm* — Lerner, David, Littenberg, Krumholz & Mentlik, LLP

(57) ABSTRACT

A radial-capitellar implant for surgical replacement of the capitellum of the humerus and, optionally, the head of the radius. The radial-capitellar implant includes a capitellar implant or surface replacement arthroplasty of the capitellum and a radial prosthesis for replacement of the head of the radius. In one embodiment the radial prosthesis includes an articular head which moveable articulates with a stem implantable in the radius.

31 Claims, 17 Drawing Sheets

(52) U.S. Cl.
CPC ............. *A61F 2002/30662* (2013.01); *A61F 2002/30663* (2013.01); *A61F 2002/30782* (2013.01); *A61F 2002/30878* (2013.01); *A61F 2002/30894* (2013.01); *A61F 2002/3809* (2013.01); *A61F 2002/3822* (2013.01); *A61F 2002/3827* (2013.01); *A61F 2220/0033* (2013.01); *A61F 2230/0019* (2013.01); *A61F 2310/00017* (2013.01); *A61F 2310/00023* (2013.01); *A61F 2310/00029* (2013.01); *A61F 2310/00407* (2013.01); *A61F 2310/00952* (2013.01)

(58) Field of Classification Search
CPC .. A61F 2002/30937; A61F 2002/30782; A61F 2002/30884
USPC ................ 623/20.11–20.13, 21.15–21.17
See application file for complete search history.

(56) References Cited

U.S. PATENT DOCUMENTS

| | | | |
|---|---|---|---|
| 3,708,805 A | 1/1973 | Scales et al. | |
| 3,813,699 A | 6/1974 | Giliberty | |
| 3,863,273 A | 2/1975 | Averill | |
| 3,868,730 A * | 3/1975 | Kaufer | A61F 2/3854 623/20.22 |
| 3,874,003 A | 4/1975 | Moser et al. | |
| 3,916,451 A * | 11/1975 | Buechel | A61F 2/3854 403/56 |
| 3,924,276 A | 12/1975 | Eaton | |
| 4,079,469 A | 3/1978 | Wadsworth | |
| 4,106,128 A | 8/1978 | Greenwald et al. | |
| 4,106,130 A | 8/1978 | Scales | |
| 4,131,957 A | 1/1979 | Bokros | |
| 4,172,296 A | 10/1979 | D'Errico | |
| 4,183,104 A | 1/1980 | Frey | |
| 4,187,559 A | 2/1980 | Grell et al. | |
| 4,224,695 A | 9/1980 | Grundei et al. | |
| 4,227,265 A | 10/1980 | Frey | |
| 4,229,840 A * | 10/1980 | Gristina | A61F 2/4261 623/21.13 |
| 4,231,121 A | 11/1980 | Lewis | |
| 4,241,463 A | 12/1980 | Khovaylo | |
| 4,242,758 A | 1/1981 | Amis et al. | |
| 4,257,129 A | 3/1981 | Volz | |
| 4,259,752 A | 4/1981 | Taleisnik | |
| 4,301,552 A | 11/1981 | London | |
| 4,309,778 A | 1/1982 | Buechel et al. | |
| 4,355,427 A | 10/1982 | Schneider | |
| 4,378,607 A | 4/1983 | Wadsworth | |
| 4,383,337 A | 5/1983 | Volz et al. | |
| 4,624,250 A | 11/1986 | Saunders et al. | |
| 4,718,414 A | 1/1988 | Saunders et al. | |
| 4,755,185 A | 7/1988 | Tarr | |
| 4,770,661 A | 9/1988 | Oh | |
| 4,784,663 A | 11/1988 | Kenna | |
| 4,801,301 A | 1/1989 | Noiles | |
| 4,822,364 A | 4/1989 | Inglis et al. | |
| 4,865,605 A | 9/1989 | Dines et al. | |
| 4,913,144 A | 4/1990 | Del Medico et al. | |
| 4,923,472 A | 5/1990 | Ugolini | |
| 4,960,427 A | 10/1990 | Noiles | |
| 5,024,670 A | 6/1991 | Smith et al. | |
| 5,030,237 A | 7/1991 | Sorbie et al. | |
| 5,147,386 A * | 9/1992 | Carignan et al. | 623/21.16 |
| 5,201,881 A | 4/1993 | Evans | |
| 5,429,641 A | 7/1995 | Gotfried | |
| 5,458,637 A | 10/1995 | Hayes | |
| 5,458,648 A | 10/1995 | Berman et al. | |
| 5,462,563 A | 10/1995 | Shearer et al. | |
| 5,489,309 A | 2/1996 | Lackey et al. | |
| 5,527,182 A | 6/1996 | Willoughby | |
| 5,527,342 A | 6/1996 | Pietrzak et al. | |
| 5,529,736 A | 6/1996 | Shalaby et al. | |
| 5,549,681 A | 8/1996 | Segmuller et al. | |
| 5,702,463 A | 12/1997 | Pothier et al. | |
| 5,702,471 A | 12/1997 | Grundei et al. | |
| 5,725,585 A | 3/1998 | Zobel | |
| 5,776,202 A | 7/1998 | Copf et al. | |
| 5,782,922 A | 7/1998 | Vandewalle | |
| 5,782,923 A | 7/1998 | Engelbrecht et al. | |
| 5,824,103 A | 10/1998 | Williams | |
| 5,824,108 A | 10/1998 | Huebner | |
| 5,879,388 A | 3/1999 | Pienkowski et al. | |
| 5,879,395 A | 3/1999 | Tornier et al. | |
| 5,888,211 A | 3/1999 | Sanders | |
| 5,906,210 A | 5/1999 | Herbert | |
| 5,910,171 A | 6/1999 | Kummer et al. | |
| 5,961,555 A | 10/1999 | Huebner | |
| 6,051,751 A | 4/2000 | Sioshansi et al. | |
| 6,059,830 A | 5/2000 | Lippincott, III et al. | |
| 6,096,083 A | 8/2000 | Keller et al. | |
| 6,126,695 A | 10/2000 | Semlitsch | |
| 6,127,596 A | 10/2000 | Brown et al. | |
| 6,159,247 A * | 12/2000 | Klawitter et al. | 623/21.15 |
| 6,162,253 A | 12/2000 | Conzemius et al. | |
| 6,217,615 B1 | 4/2001 | Sioshansi et al. | |
| 6,217,616 B1 | 4/2001 | Ogilvie | |
| 6,270,503 B1 | 8/2001 | Schmieding | |
| 6,270,529 B1 | 8/2001 | Terrill-Grisoni et al. | |
| 6,281,264 B1 | 8/2001 | Salovey et al. | |
| 6,290,725 B1 | 9/2001 | Weiss et al. | |
| 6,299,645 B1 | 10/2001 | Ogden | |
| 6,306,171 B1 | 10/2001 | Conzemius | |
| 6,361,563 B2 | 3/2002 | Terrill-Grisoni et al. | |
| 6,379,388 B1 | 4/2002 | Ensign et al. | |
| 6,383,223 B1 * | 5/2002 | Baehler | A61F 2/4241 623/16.11 |
| 6,425,921 B1 | 7/2002 | Grundei et al. | |
| 6,527,808 B1 | 3/2003 | Albertorio et al. | |
| 6,547,824 B1 | 4/2003 | Price | |
| 6,656,225 B2 | 12/2003 | Martin | |
| 6,709,459 B1 | 3/2004 | Cooney, III et al. | |
| 6,709,461 B2 | 3/2004 | O'Neil et al. | |
| 6,767,368 B2 | 7/2004 | Tornier | |
| 6,811,568 B2 | 11/2004 | Minamikawa | |
| 6,818,019 B2 | 11/2004 | Horber | |
| 7,160,329 B2 | 1/2007 | Cooney, III et al. | |
| 7,169,186 B2 | 1/2007 | Harris et al. | |
| 7,238,207 B2 | 7/2007 | Blatter et al. | |
| 7,247,170 B2 * | 7/2007 | Graham | A61F 2/3804 623/20.13 |
| 7,452,381 B2 | 11/2008 | Steinmann | |
| 7,608,110 B2 | 10/2009 | O'Driscoll | |
| 7,662,185 B2 | 2/2010 | Alfaro et al. | |
| 7,740,661 B2 | 6/2010 | Baratz et al. | |
| 7,749,277 B2 | 7/2010 | McLean | |
| 7,799,086 B2 | 9/2010 | Justin et al. | |
| 7,875,082 B2 | 1/2011 | Naidu | |
| 8,034,116 B2 | 10/2011 | Vander Meulen et al. | |
| 8,066,779 B2 | 11/2011 | Gibbs et al. | |
| 8,110,005 B2 | 2/2012 | Berelsman et al. | |
| 8,114,163 B2 | 2/2012 | Berelsman et al. | |
| 8,366,781 B2 | 2/2013 | Berelsman et al. | |
| 8,425,615 B2 | 4/2013 | Berelsman et al. | |
| 8,535,382 B2 | 9/2013 | Kehres et al. | |
| 2002/0065561 A1 * | 5/2002 | Ogilvie et al. | 623/21.15 |
| 2003/0014123 A1 * | 1/2003 | Copf | A61F 2/30771 623/23.14 |
| 2003/0040805 A1 | 2/2003 | Minamikawa | |
| 2003/0093156 A1 | 5/2003 | Metzger et al. | |
| 2003/0208276 A1 | 11/2003 | Berelsman et al. | |
| 2003/0208280 A1 | 11/2003 | Tohidi | |
| 2004/0030394 A1 | 2/2004 | Horber | |
| 2004/0078083 A1 | 4/2004 | Gibbs et al. | |
| 2004/0122519 A1 | 6/2004 | Wiley et al. | |
| 2004/0220678 A1 | 11/2004 | Chow et al. | |
| 2004/0220679 A1 | 11/2004 | Diaz et al. | |
| 2005/0033436 A1 * | 2/2005 | Schlapfer et al. | 623/17.14 |
| 2005/0033442 A1 | 2/2005 | Fisher et al. | |
| 2005/0049710 A1 | 3/2005 | O'Driscoll et al. | |

(56) References Cited

U.S. PATENT DOCUMENTS

| | | | |
|---|---|---|---|
| 2005/0075735 A1 | 4/2005 | Berelsman et al. | |
| 2006/0064173 A1 | 3/2006 | Guederian | |
| 2006/0100715 A1* | 5/2006 | De Villiers | 623/23.4 |
| 2006/0142866 A1* | 6/2006 | Baratz | A61F 2/3804 623/20.11 |
| 2006/0173546 A1 | 8/2006 | Berelsman et al. | |
| 2006/0229732 A1 | 10/2006 | Bachelier | |
| 2008/0288079 A1 | 11/2008 | Leibel | |
| 2010/0087928 A1 | 4/2010 | Graham et al. | |
| 2010/0241236 A1 | 9/2010 | Katrana et al. | |
| 2011/0144759 A1 | 6/2011 | Berelsman et al. | |
| 2012/0109323 A1 | 5/2012 | Berelsman et al. | |
| 2012/0221113 A1 | 8/2012 | Katrana et al. | |
| 2013/0333198 A1 | 12/2013 | Kehres et al. | |

FOREIGN PATENT DOCUMENTS

| | | |
|---|---|---|
| JP | 4170948 B2 | 10/2008 |
| WO | 0042944 | 7/2000 |
| WO | 0042944 A1 | 7/2000 |
| WO | 2004026185 | 4/2004 |
| WO | 2008/098250 A2 | 8/2008 |

OTHER PUBLICATIONS

Judet, T. et al., Radial-head Prosthesis Indications and Techniques, pp. 1-14, unknown date.
Liverpool™, Radial Head Replacement Operative Technique, BIOMET Orthopedics, Inc., pp. 1-5, copyright 2002.
Surgical Technique, rHead Recon™ Radial Implant System, Avanta Orthopaedics, pp. 1-13, copyright 2002.
Swanson, Alfred B., Swanson Titanium Radial Head Implant Regular and Narrow Stem, pp. 1-8, Grand Rapids, Michigan, copyright 2002.
U.S. Appl. No. 12/029,429 to David Leibel, filed Feb. 11, 2008.
Extended European Search Report from European Patent Application No. 05825602.5, dated Sep. 4, 2008.
Search Report for European divisional patent application N° EP 10 194806.5, dated Mar. 17, 2011.
Japanese Office Action for Japanese patent application 2007-544418.
International Search Report dated Mar. 30, 2006 for PCT/US2005/042945.
Supplementary Partial European Search Report dated Aug. 26, 2008 for EP05825602.
Small Bones Innovations, Inc., rHead™ Family Radial Head Implant System, 2009.

* cited by examiner

RADIAL-CAPITELLAR IMPLANT

STATEMENT OF RELATED APPLICATIONS

This application is a continuation of U.S. application Ser. No. 11/001,662, filed on Dec. 1, 2004 (allowed), which is hereby incorporated by reference in its entirety.

FIELD OF THE INVENTION

The invention relates generally to the field of joint replacement prostheses for the human body. More specifically, the invention relates to joint replacement prostheses for the human elbow.

BACKGROUND OF THE INVENTION

The elbow is formed at the meeting of the distal end of the humerus and the proximal ends of the radius and ulna. In the elbow, the head of radius articulates with the capitellum of the humerus and radial notch of the ulna. The trochlear notch of the ulna articulates with the trochlea of the humerus. When the forearm is in extreme flexion, the head of the radius fits into the radial fossa located just above the capitellum. The lateral epicondyle is found on the lateral aspect of the humerus just above the capitellum. The lateral epicondyle serves as the insertion for one portion of the supinator muscle which attaches at about the proximal third of the radius.

Along their lengths the radius and ulna are joined by the interosseous ligament, also known as the interosseous membrane. The interosseous ligament has a fibrous structure that is oriented on a bias relative to the axis of the forearm. This ligamentous interconnection between the radius and the ulna serves to transfer loads at the wrist from the radius to the ulna. At the wrist, the distal end of the radius is a larger and more robust structure than the head of the ulna. Thus, at the wrist a large share of the load carried by the hand is transferred to the radius. However, at the elbow, the ulna is substantially larger than the head of the radius. The interosseous ligament serves to transfer loads from the radius to the ulna so that the load is substantially equalized at the elbow or so the load is carried more by the ulna than the radius. The loading distribution between the radius and the ulna at the humeral articulation is dynamic, varying with the position and motion of the forearm and hand.

The radial head is an important component of normal elbow and forearm function. The radial head contributes to both the radiocapitellar and proximal radioulnar joints.

The radial head makes a 12 to 15 degree lateral angle to the radial shaft. This lateral angle is away from the radial tuberosity which is located distal to the radial head on the medial side of the radius. Various ligaments about the radial head provide important soft tissue support and are essential to elbow stability. The stress distribution at the elbow varies in pronation and supination but averages about 60 percent to the radiohumeral joint and about 40 percent at the ulnar humeral articulation.

The radial head can be damaged in many ways. One common source of damage the head of the radius is a fall onto an outstretched hand. Historically, if the radial head was damaged so severely as to be impossible to repair with the use of bone screws or other internal fixation structures, the radial head was resected and the elbow closed. Radial head resection was sometimes necessary due to fracture, osteochondrosis or secondary arthritis. Unfortunately, radial head resection tends to cause significant adverse effects on elbow and forearm function.

Resection of the radial head tends to cause persistent elbow instability following elbow fracture, dislocation, rotational instability injuries and medial lateral translation injuries. Excision of the radial head can also cause forearm axial instability, particularly if the remaining stabilizing structures have been compromised. Since the radial head acts as a secondary stabilizer to the elbow joint, once the radial head is removed the soft tissue stabilizers including the collateral ligaments, the interosseous membrane and the articular surfaces of the radial ulnar joints may be compromised and the instability of the joint tends to increase. Thus, replacement of the radial head with an implant has been embraced as a way to attempt to restore anatomic normalcy and functional usefulness to the elbow and forearm.

Radial head implants exist in the art. Typically, radial head implants are available in multiple sizes to approximate anthropomorphic differences in radial head size in different patients. A radial head implant generally will include a radial head component and a stem component. The radial head component is designed to anatomically articulate with the convexity of the capitellum for an anatomic joint surface contact area. The circumference of the head matches the normal radioulnar joint articulation, preserves the annular ligament and minimizes release for exposure of important lateral ulnar collateral ligament. The radial head and radial stem may be joined together by a Morse tapered protrusion that is adapted to interface with a Morse tapered cavity. Generally, the Morse tapered cavity is located in the head which allows placement of the radial head onto the protrusion on the radial stem.

A typical radial prosthesis has a stem configured for implantation into the intramedullary canal of the proximal radius. Some types of radial head implant include a limited ball joint articulation between the radial head component and the stem component. These are sometimes known as bipolar implants. In this type of implant, the concave articular surface of the radial head anatomically articulates with the convexity of the capitellum while the radial head articulates with the stem of the implant. This allows the use of a radial head implant in situations where the radial head may be damaged in such a way as to make implantation of a fixed radial head implant difficult or impossible. Use of a bipolar radial head implant allows for some adjustment of the head of the implant with the capitellum once the implant is in place. The articulation between the head and the stem allows for the correction of angular alignment deformities between the radius and the capitellum. The ball and socket design of this type of radial head implant allows radial-capitellar contact to be maintained through a functional range of flexion and forearm rotation.

Unfortunately, some falls onto an outstretched hand will also damage the capitellum of the humerus. In addition, the capitellum is sometimes to subject to arthritic degeneration or increased wear after placement of a radial head implant.

As discussed above, sometimes resection of the radial head is performed without an implant. Resection of the radial head leaves the patient with a so-called ulna plus variation which tends to lead to wrist pain which, in turn, can be debilitating. For these reasons, it would be beneficial to the patient to be able to surgically replace and restore the capitellum as well as the radial head.

Traumatic injury of the radioulnar joint is common. Injuries to the radioulnar joint include radial head fractures and radial head fractures associated with ligament injuries;

combined proximal ulna fracture with radial dislocation or fracture; radial head fracture associated with dislocation of the elbow; and forearm and elbow injuries in combination. Forearm and elbow injuries include radial head fracture combined with interosseous membrane disruption, the so-called Essex-Lopresti lesion. In the case of an Essex-Lopresti lesion or interosseous ligament tear, the transfer of loads from the hand and then from the radius to the ulna is compromised. This lack of transfer from the radius to the ulna creates an increased load at the radial head where it meets the capitellum which increases wear on the capitellum as well as the radial head.

Thus, it would be beneficial to the orthopedic arts to have an implant available to surgically repair damage to the capitellum as well as to the head of the radius.

SUMMARY OF THE INVENTION

The present invention solves many of the above mentioned problems by making available a radial-capitellar implant including a capitellar implant to be implanted into the distal end of the humerus. The invention may also include a capitellar implant to replace the capitellum of the humerus in combination with a radial head implant to replace the head of the radius and to articulate with the capitellar implant. Another aspect of the invention includes a capitellar implant and a bipolar radial head implant in which the head of the radial head implant includes an articulated head that can conically, rotationally, articulate relative to the stem of the radial prosthesis to replace the head of the radius.

The capitellar implant of the present invention generally includes a body and a stem. The body of the capitellar implant defines a convex articular face. The convex articular face may have a spherical surface and extends about one hundred thirty five to one hundred forty degrees. The capitellar implant further includes a flat on its medial side and a curved flat on its lateral side. The curved flat on the lateral surface allows for excursion of the radial nerve over the lateral surface of the implant. The curved flat also facilitates the smooth gliding of the joint capsule and ligamentous structures over the implant during flexion/extension and pronosupinatory motions. The convex articular face allows articulation of the capitellar implant with the head of the radius over an arc of approximately one hundred thirty five to one hundred forty degrees to allow full range of motion in flexion and extension of the forearm.

The stem of the capitellar implant is offset approximately 10 degrees to the medial side. The stem may be substantially square in cross section and tapered to a substantially square end. The stem of the capitellar implant may be treated to encourage osseointegration such as by application of titanium plasma coating.

The side of the capitellar implant from which the stem extends includes a bone interface surface which may have two flat facets. The flat facets are angled relative to one another at an angle of approximately 135 degrees.

In another embodiment, the invention includes both the capitellar implant as described above and a radial prosthesis for implantation to replace the natural head of the radius where it articulates with the capitellum and the ulna. In one embodiment of the invention, the radial head implant includes a stem and a head.

The head of the radial head implant defines a concave articular surface that may be formed of ultra high molecular weight polyethylene (UHMWPE) or another durable self-lubricating material. The head further includes a stem interface portion which defines a substantially cylindrical cavity into which a portion of the stem inserts. The cavity may be formed with a morse tapered fit to allow ease of placement of the head onto the stem. The portion of the stem of the radial head implant that is inserted into the intramedullary canal in this embodiment has a smooth continuous surface and a bend forming an angle which occurs about midway down the length of the stem. The stem further includes a collar which abuts the head of the radial head implant along with the morse tapered extension to form the interface between the head and the stem.

In another embodiment, the radial head implant includes a head and a stem that are joined by a ball and socket joint to allow for correction of angular alignment deformities of up to about ten degrees. In this embodiment, the radial head implant includes a head with a concave articular surface that is lined with ultra high molecular weight polyethylene or another durable self-lubricating material, an intermediate portion and a secondary articular portion which articulates with the stem. The intermediate portion is typically formed of cobalt chromium stainless steel, titanium or another biocompatible metal. The secondary articular portion includes a female ball and socket interface and a male ball and socket interface to interface with the radial prosthesis stem.

Alternately, the articular portion and the intermediate portion can be formed as a single piece formed from UHMWPE or another durable self lubricating material. In this situation, the head of the radial prosthesis includes a female ball and socket interface and a male ball and socket interface to interface with the radial prosthesis stem as well as a concave articular face to articulate with the capitellar implant.

The stem of this embodiment includes a stem with a collar similar to that described above as well as a spheroidal ball protruding from the stem and extending from the collar in a direction opposite the stem. The spheroidal protrusion rests in a spheroidal female cavity. The female cavity accepts the male portion of the ball joint of the head portion and the spheroidal protrusion inserts into the female ball and socket portion of the head of the radial head implant. This structure increases the contact area between the articular head and the articular stem improving the wear characteristics and distributing loading over a larger area. In this embodiment of the invention the stem may also be treated to encourage osseointegration such as by application of a commercially pure titanium plasma coating.

DETAILED DESCRIPTION OF THE INVENTION

Figure 1:
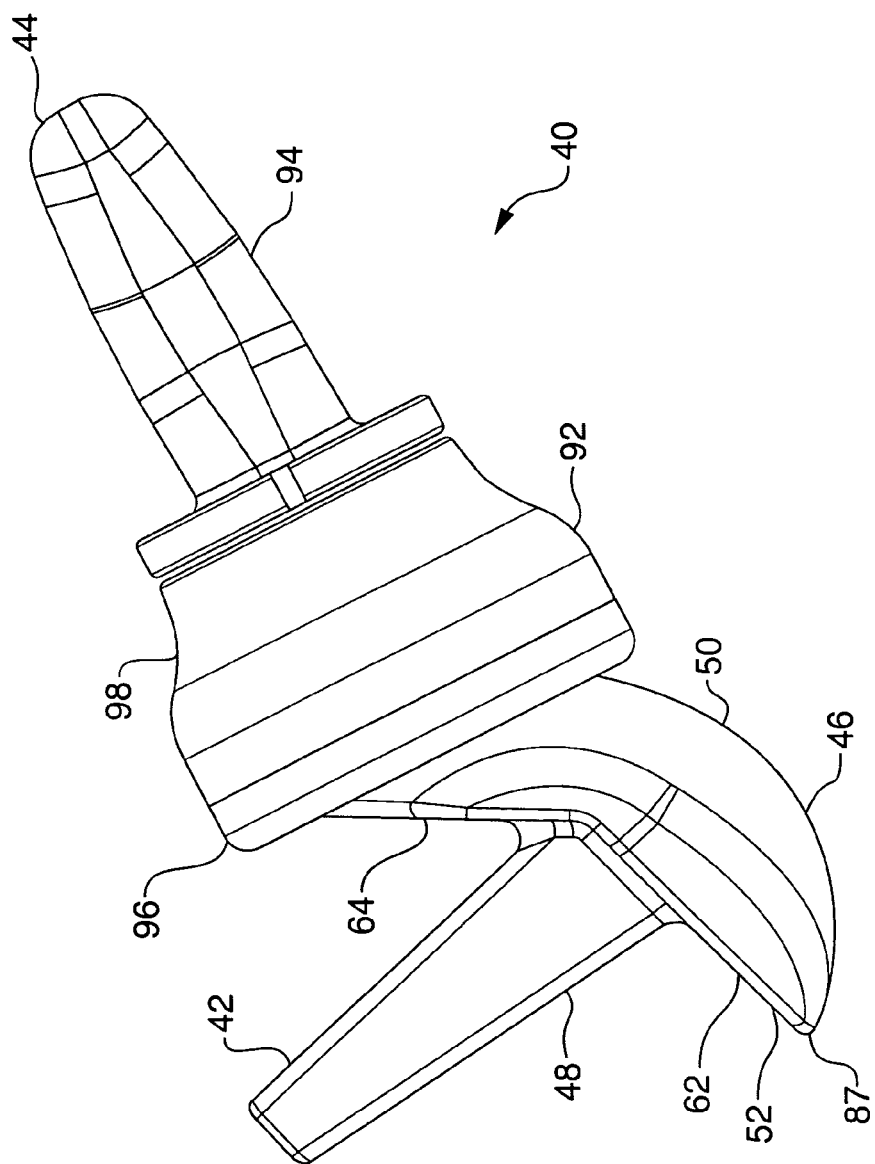
FIG. 1 is a plan view of the radial-capitellar implant in accordance with the present invention in a flexed position.
Figure 2:
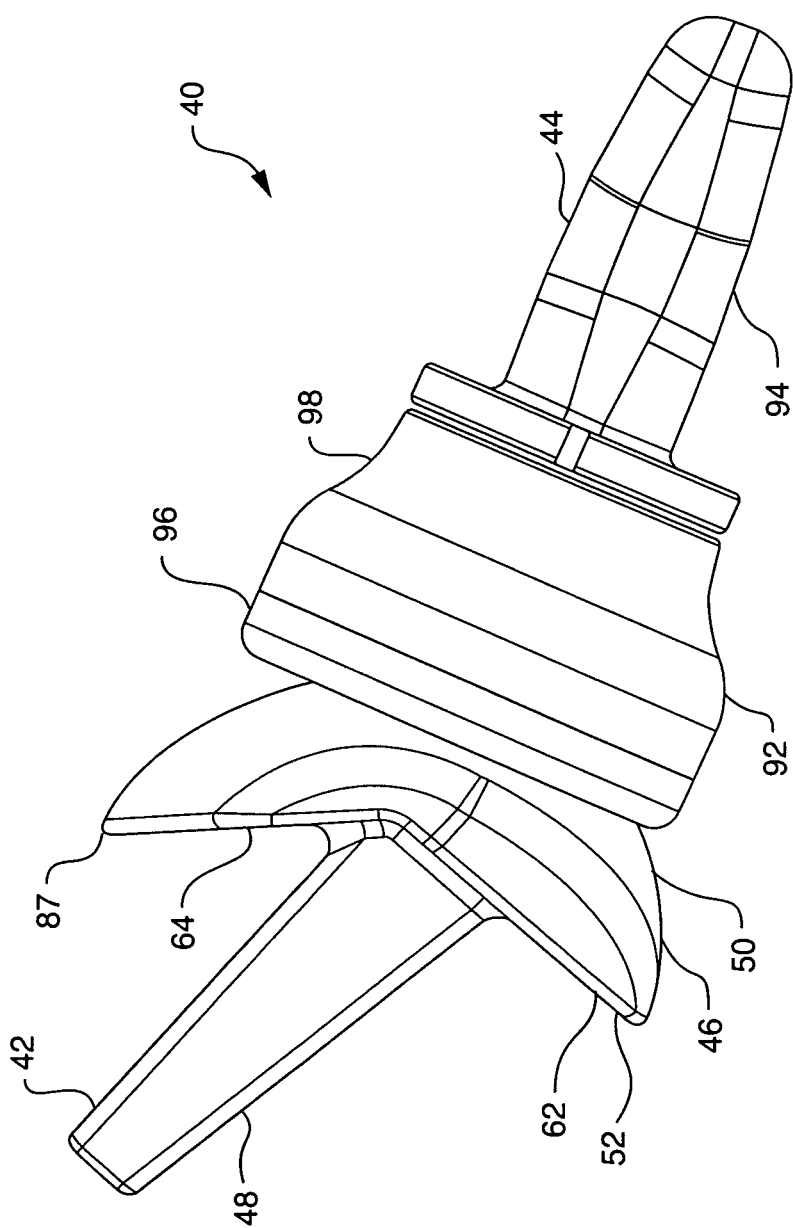
FIG. 2 is a plan view of the radial-capitellar implant in a partially extended position.
Figure 3:
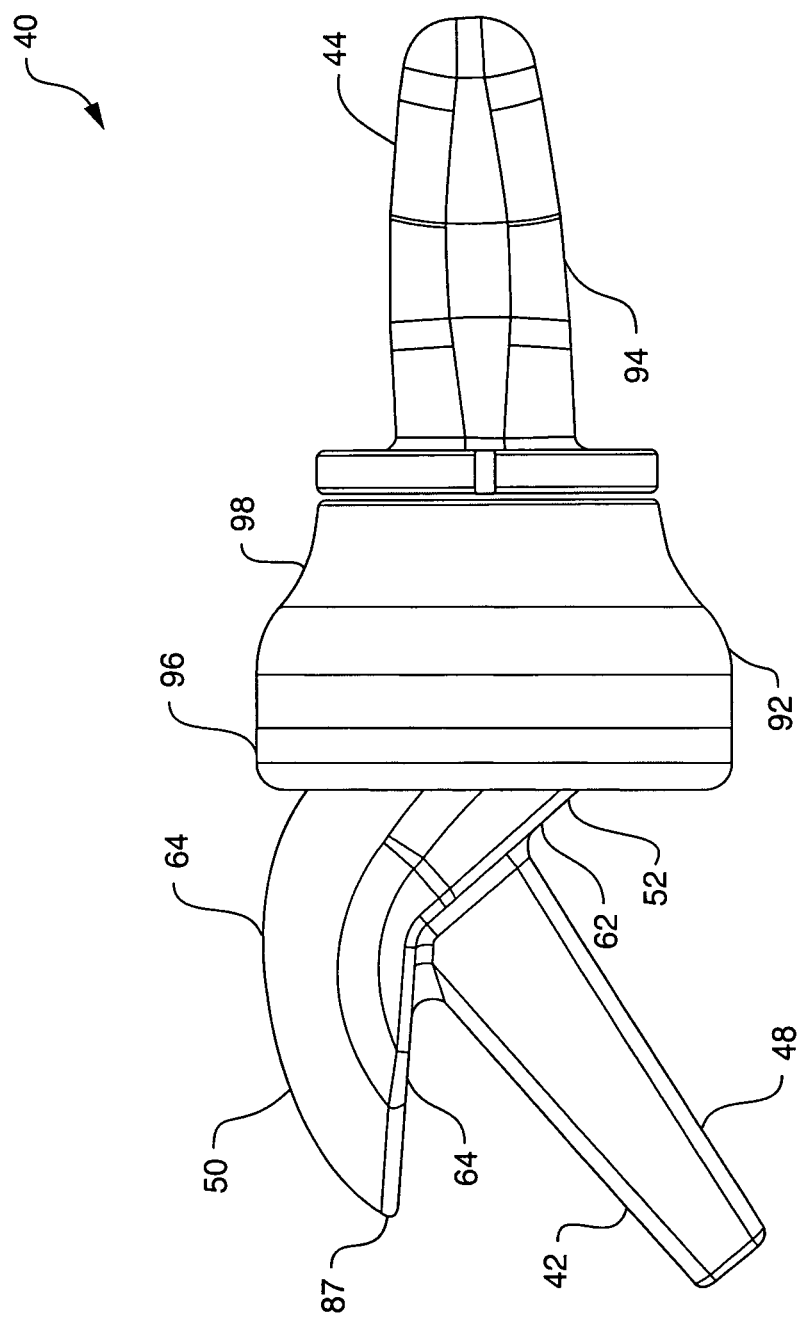
FIG. 3 is a plan view of the radial-capitellar implant in a fully extended position.
Figure 4:
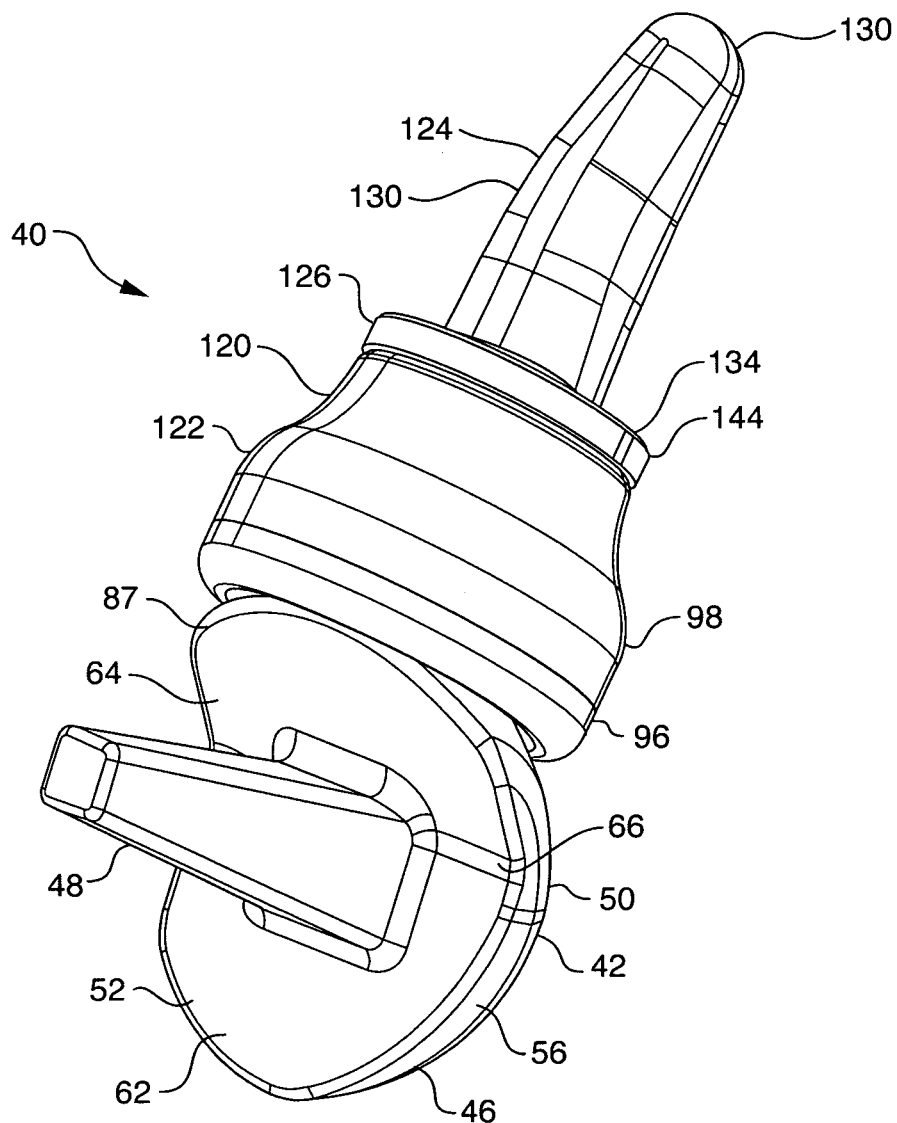
FIG. 4 is a perspective view of the radial-capitellar implant in a flexed position.
Figure 5:
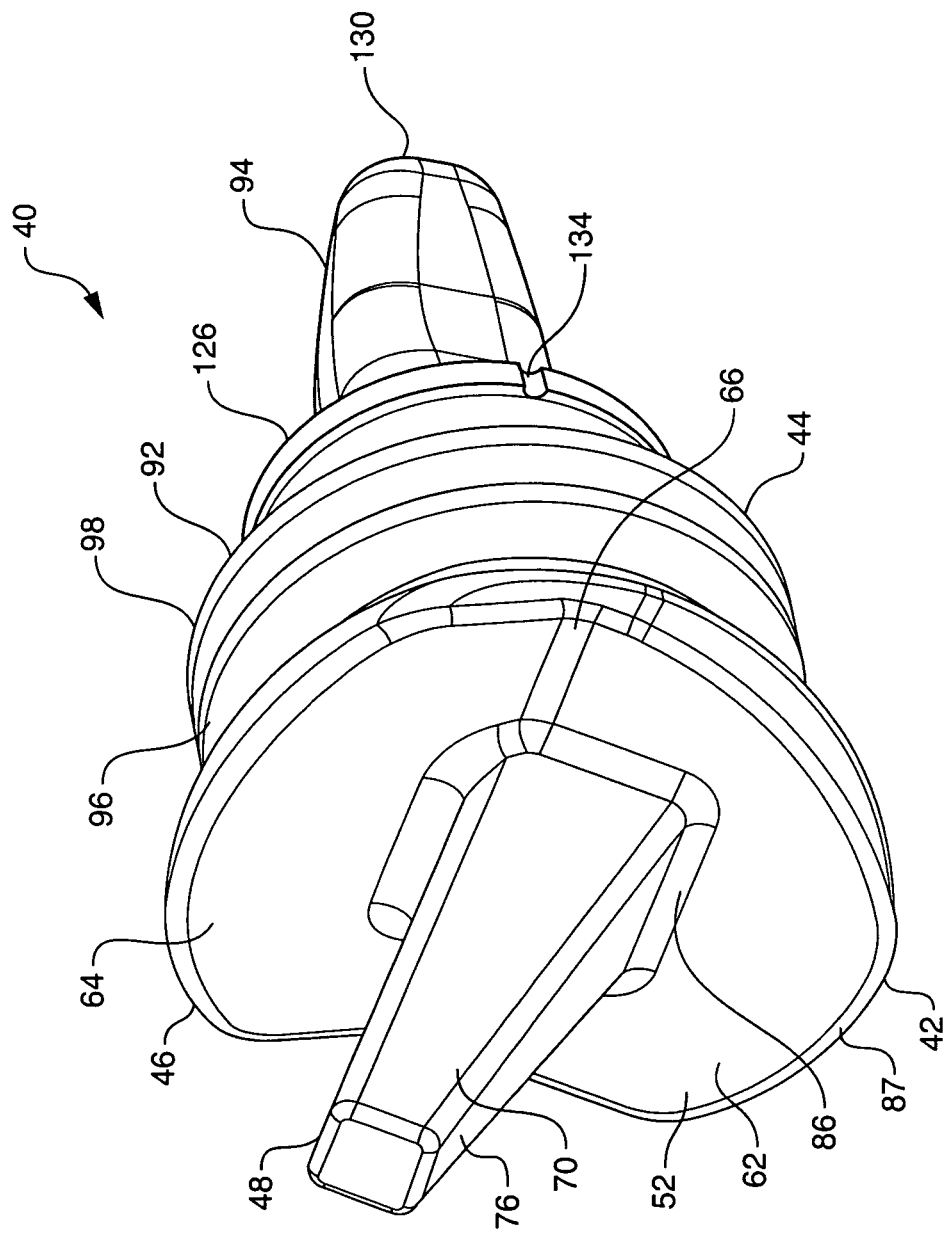
FIG. 5 is a perspective view of the radial-capitellar implant in a partially extended position.
Figure 6:
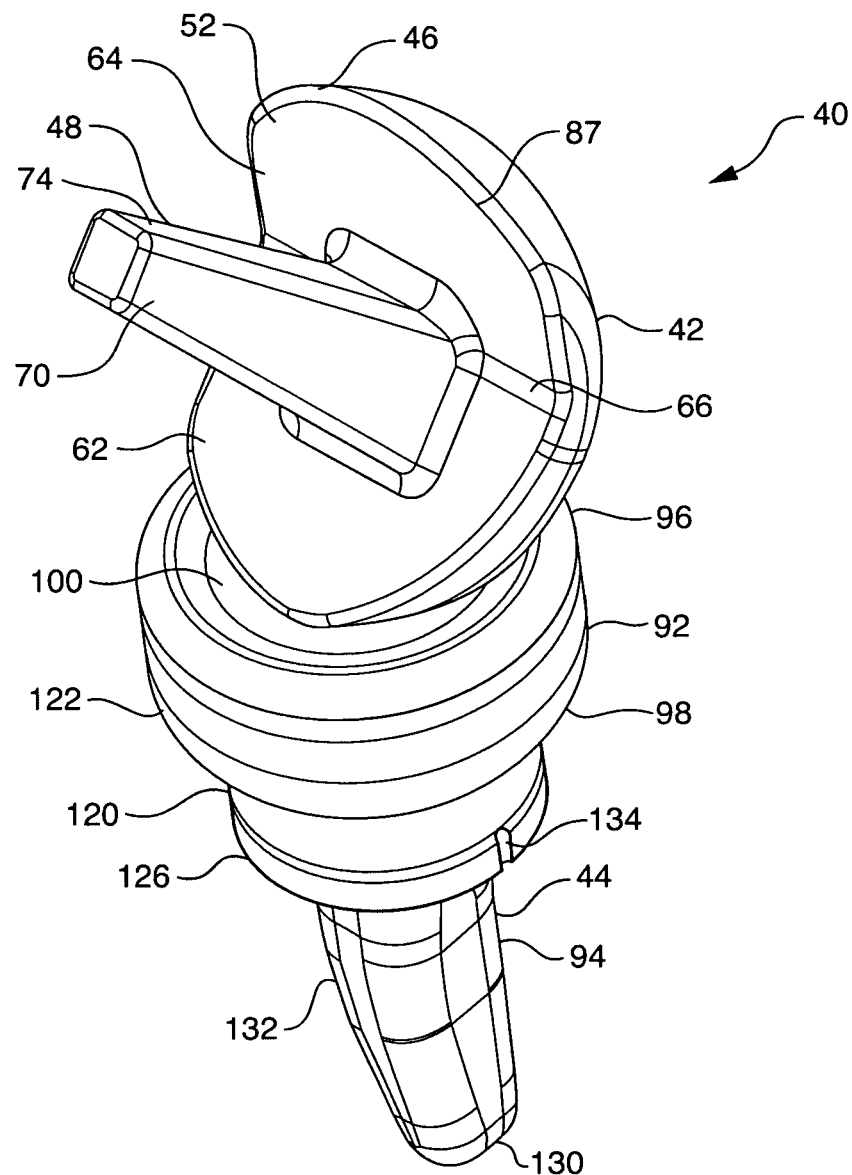
FIG. 6 is a perspective view of the radial-capitellar implant in a fully extended position.

The radial-capitellar implant 40 of the present invention generally includes capitellar prosthesis 42 and radial prosthesis 44. Referring initially to FIGS. 1-5 capitellar prosthesis 42 and radial prosthesis 44 are shown in various views as articulated with one another in various degrees of flexion and extension.

Referring particularly to FIGS. 1-6 and 11-16 capitellar prosthesis 42 generally includes body 46 and stem 48. Stem 48 is joined to body 46 extending outwardly from bone interface surface 52 of body 46. Articular face 50 presents a substantially spheroidal surface. Body 46 and stem 48 may be integrally formed from a single piece of material such as by casting or machining.

Articular face 50 is smooth and may be mirror polished to facilitate smooth articulation. Articular face 50 may present a substantially spheroidal convex surface Articular face 50 extends over an arc of approximately 170 to 190 degrees in a first direction and an arc of 80 to 100 degrees in a second direction generally perpendicular to the first direction. In one embodiment, articular face 50 extends along an arc of about 170 to about one 190 in a first direction and along an arc of about 80 to about 100 degrees in a second direction, the second direction being substantially normal to the first direction. Articular face 50 further presents medial flat 54 and lateral curved flat 56. Lateral curved flat 56 presents straight portion 58 and curved portion 60. Lateral curved flat 56 allows for excursion of the radial nerve over the lateral aspect of articular face 50.

Bone interface surface 52 presents a first facet 62 and a second facet 64. First facet 62 and second facet 64 meet at juncture 66 and form an obtuse angle 68 of approximately 130 to 150 degrees.

Stem 48 extends outwardly away from bone interface surface 52 substantially at juncture 66.

Stem 48 may be substantially square in cross section and presents lateral side 70, medial side 72, superior side 74 and inferior side 76. These designations correspond to the positions of the sides when capitellar prosthesis 42 is implanted in the humerus. Stem 48 extends outwardly from bone interface surface 52 and is angled medially relative to bone interface surface 52. All corners 90 of stem 48 may be radiused.

Desirably medial side 72 of stem 48 displays bend 78. Thus medial side 72 presents proximal surface 80 proximal to bend 78 and distal surface 82 distal to bend 78. Proximal surface 80 forms an angle with first facet 62 of approximately ninety five degrees. A centerline of stem 48 is angled approximately ten degrees from a perpendicular extending outwardly from first facet 62. Distal surface 82 of medial side 72 is angled approximately three degrees relative to the centerline of stem 48. Lateral side 70 of stem 48 is angled approximately five degrees relative to the centerline of stem 48. Stem 48 presents a substantially quadrilateral distal end 84. Superior side 74 of stem 48 is angled approximately two degrees relative to a centerline of stem 48. Inferior side 76 of stem 48 is angled approximately eight degrees relative to centerline of stem 48. Stem 48 and bone interface surface 52 meet at fillet 86. Articular face 50 and bone interface surface 52 meet at edges 87. Edges 87 are radiused around the perimeter 88 of articular face 50 and bone interface surface 52 where articular face 50 and bone interface surface 52 meet.

Capitellar prosthesis 42 is formed of cobalt chrome alloy per ASTM F-1537 or another biocompatible, corrosion resistant material. Capitellar prosthesis 42 is desirably a unitary structure formed from a single piece of material. Bone interface surface 52 and stem 48 may be roughened to encourage osseointegration such as by commercially pure titanium plasma coating.

Figure 7:
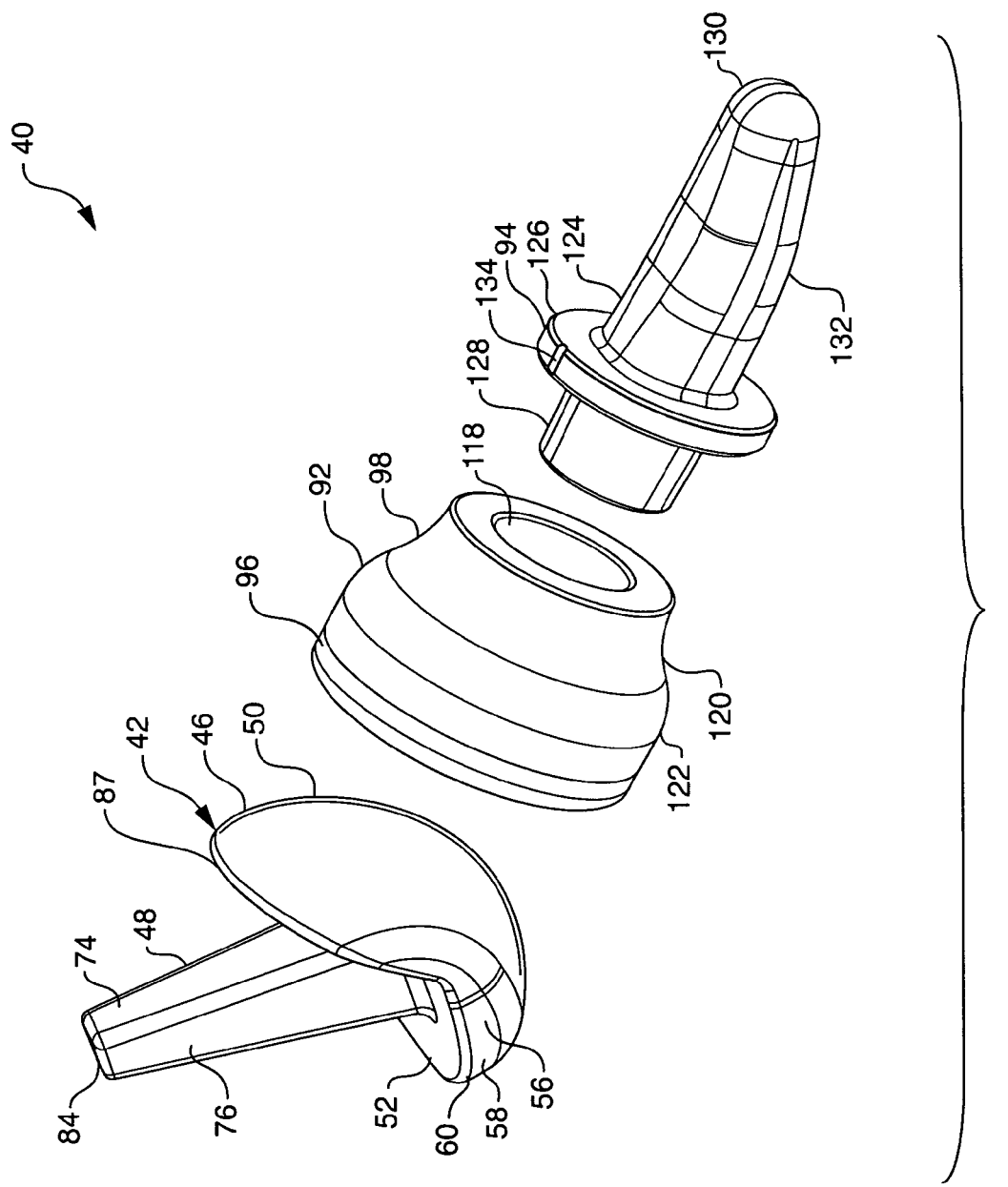
FIG. 7 is an exploded perspective view of the radial-capitellar implant.
Figure 8:
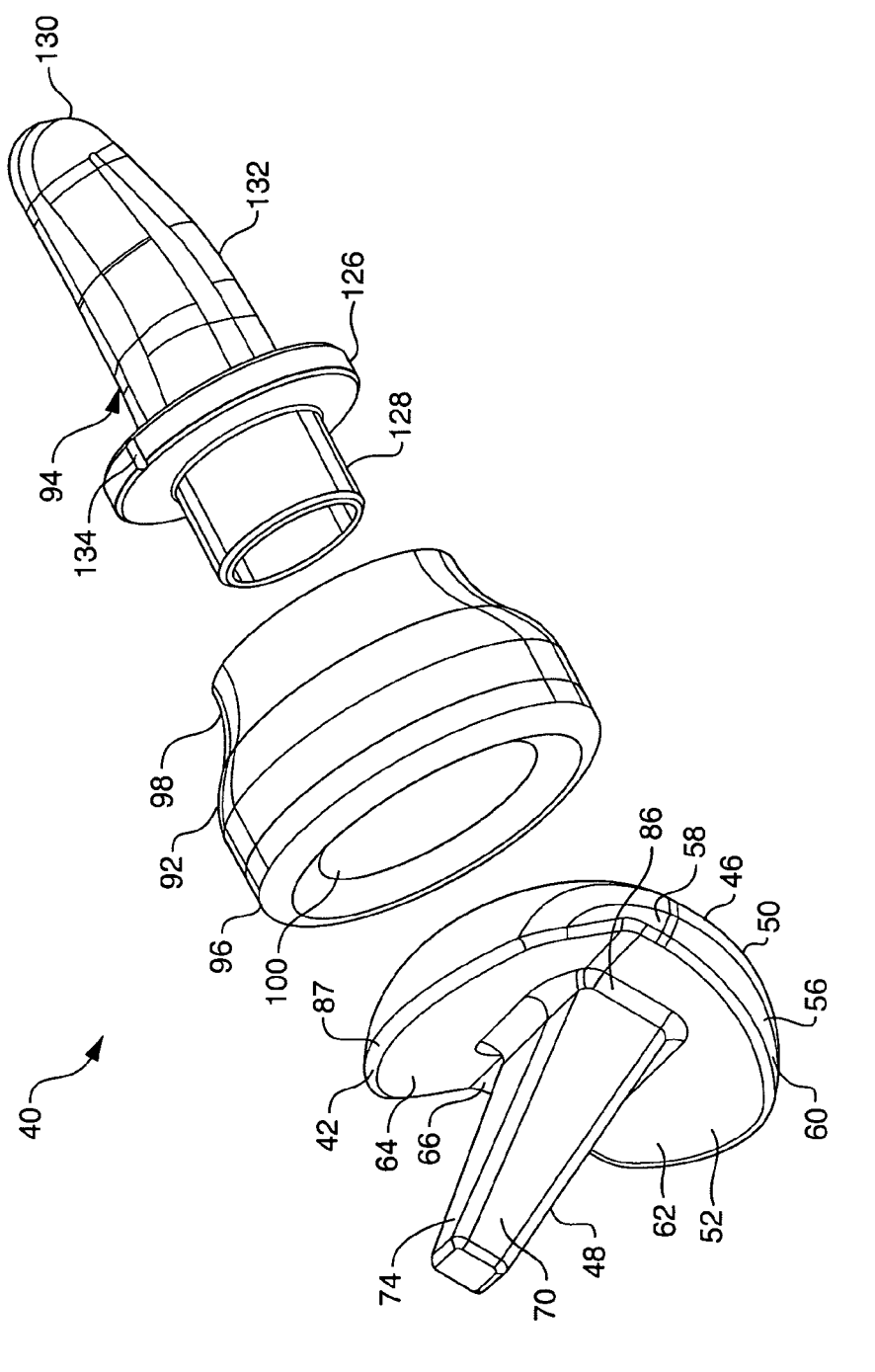
FIG. 8 is another exploded perspective view of the radial-capitellar implant.
Figure 9:
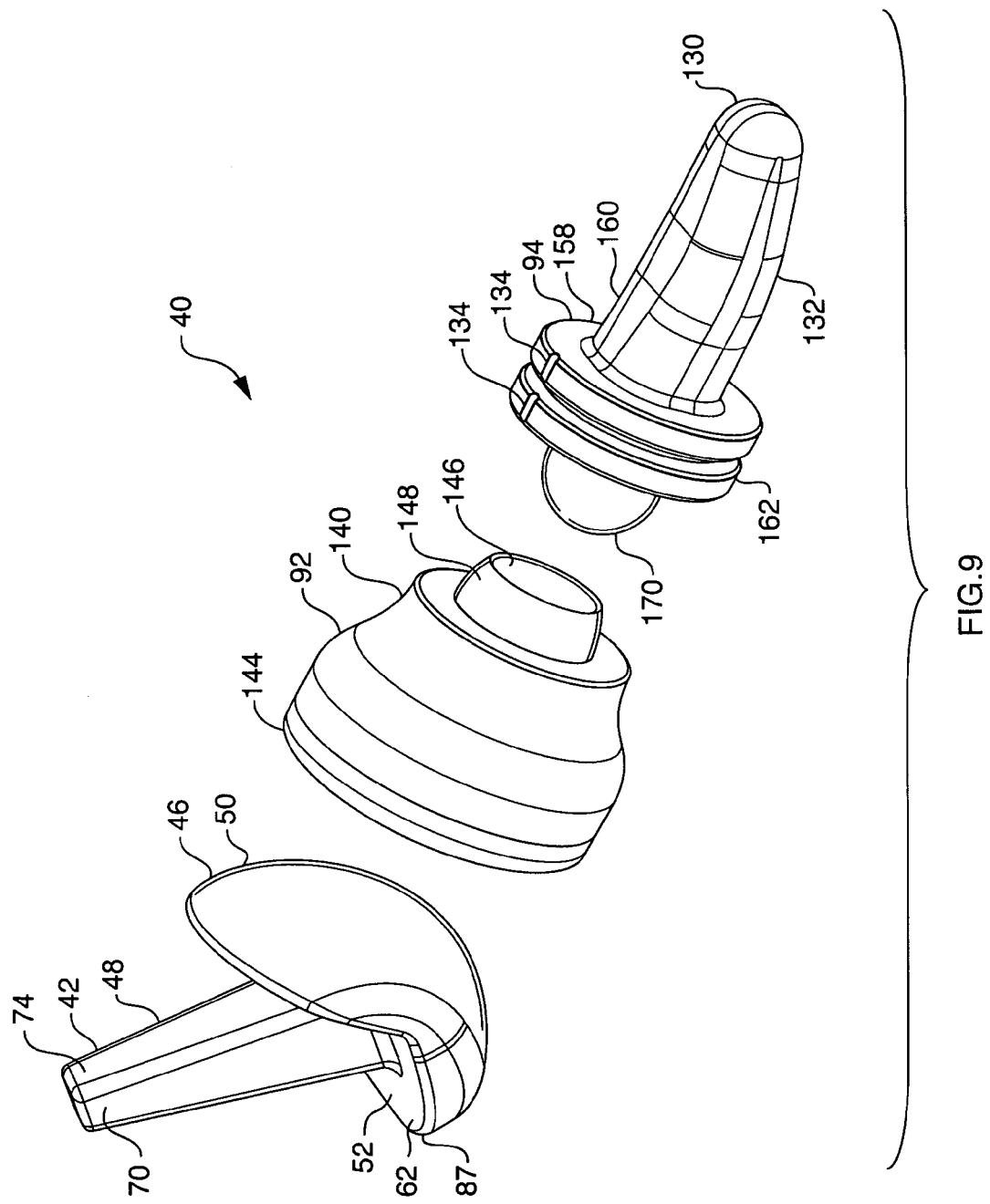
FIG. 9 is an exploded perspective view of another embodiment of the radial-capitellar implant.
Figure 10:
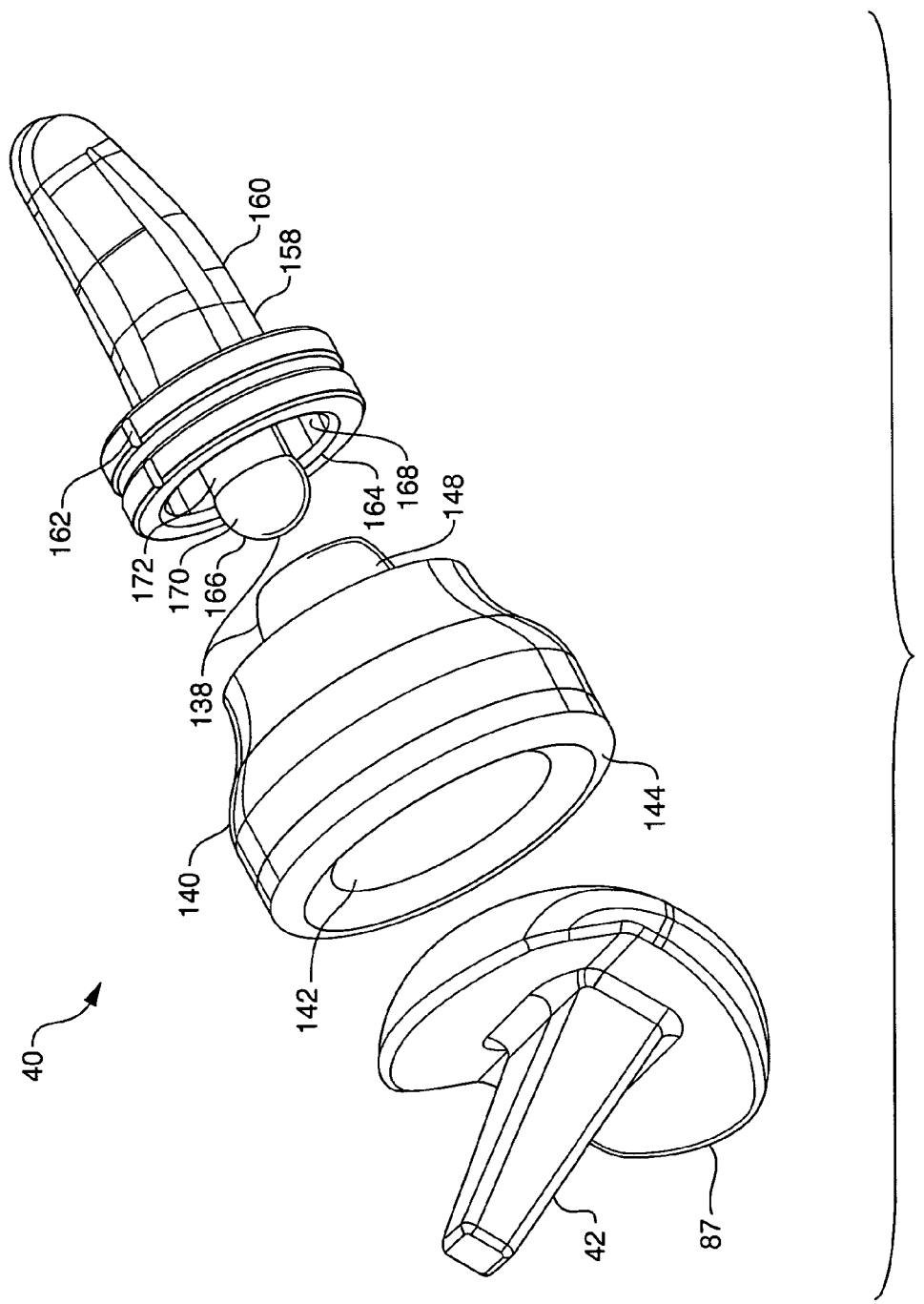
FIG. 10 is an additional exploded perspective view of the radial-capitellar implant.
Figure 11:
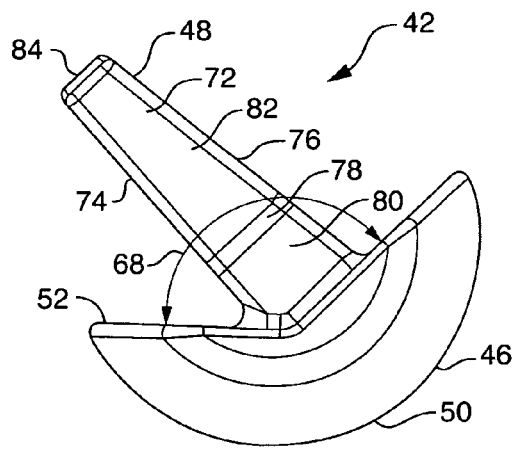
FIG. 11 is an elevational view of a capitellar implant in accordance with the present invention.
Figure 12:
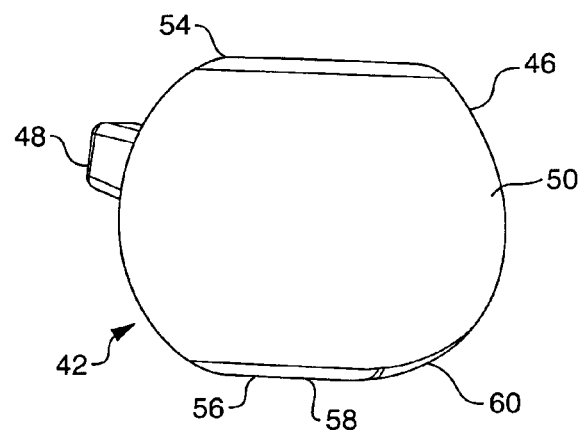
FIG. 12 is a plan view of the capitellar implant.
Figure 13:
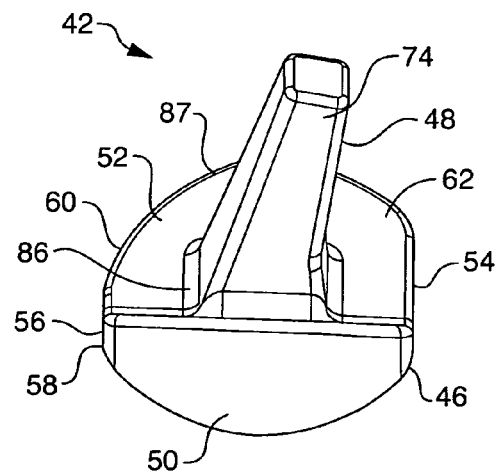
FIG. 13 is a front elevational view of the capitellar implant.
Figure 14:
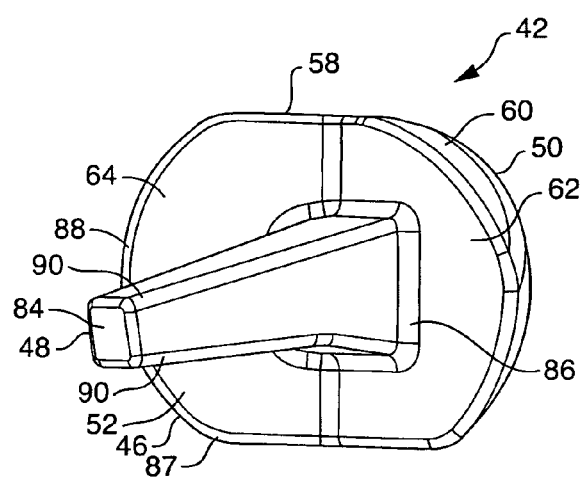
FIG. 14 is a perspective view of the capitellar implant.
Figure 15:
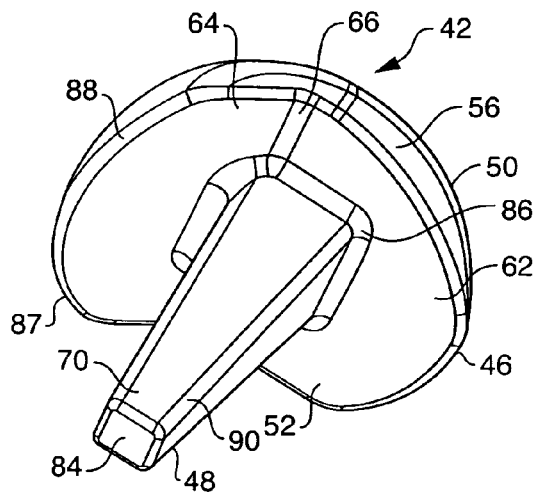
FIG. 15 is another perspective view of the capitellar implant.
Figure 16:
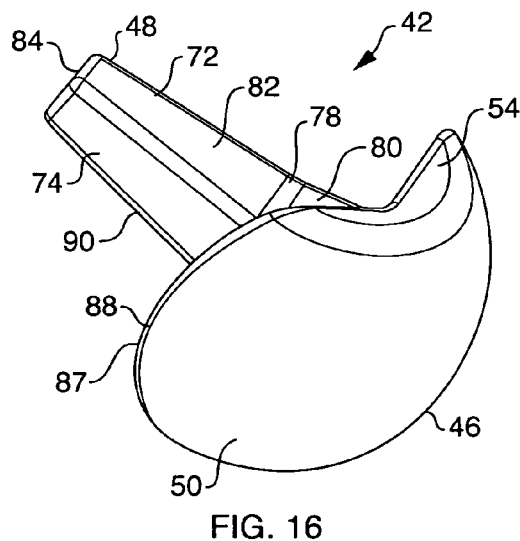
FIG. 16 is another perspective view of the capitellar implant.
Figure 17:
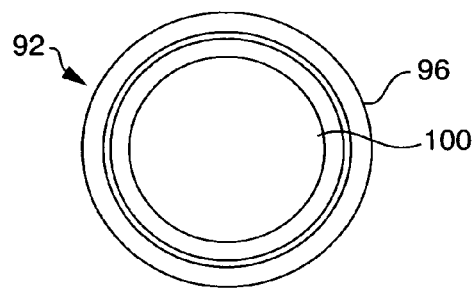
FIG. 17 is a plan view of the head of the radial implant.
Figure 18:
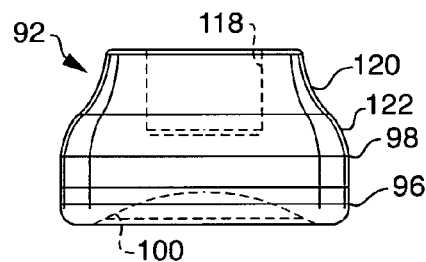
FIG. 18 is a sectional view of the head of the radial implant.
Figure 19:
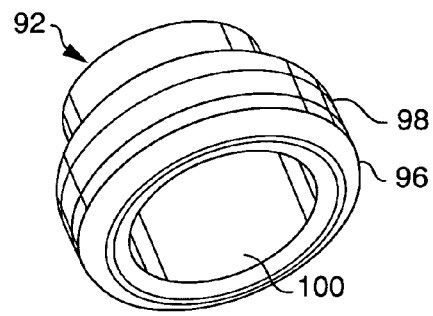
FIG. 19 is a perspective view of the head of the radial implant.
Figure 20:
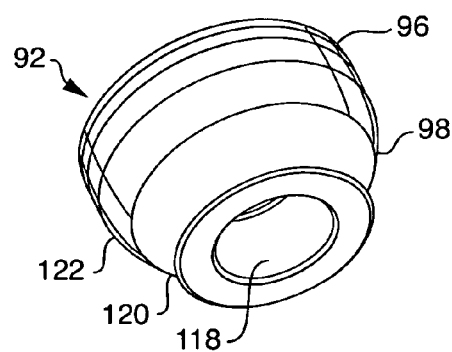
FIG. 20 is a perspective view of the head of the radial implant.
Figure 21:
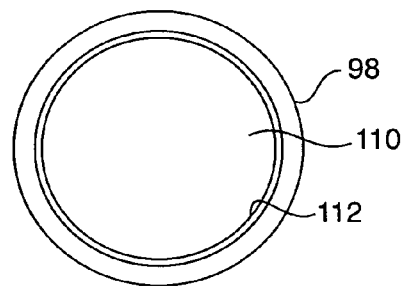
FIG. 21 is a plan view of a stem interface component of the head of the radial implant.

Referring particularly to FIGS. 7 and 8, one embodiment of radial prosthesis 44 generally includes head 92 and stem 94. Referring particularly to FIGS. 17-25, head 92 generally includes articular portion 96 and stem interface portion 98.

Referring particularly to FIGS. 25-28 articulation portion 96 of radial prosthesis 44 may be formed of UHMWPE or another durable self-lubricating material. Other polymers, composites or metals may also be suitable.

Figure 26:
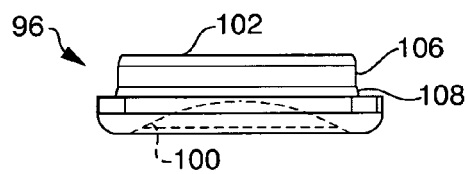
FIG. 26 is a sectional view of the capitellar interface portion showing internal structures in phantom.
Figure 27:
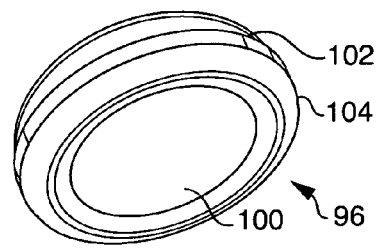
FIG. 27 is a perspective view of the capitellar interface portion.
Figure 28:
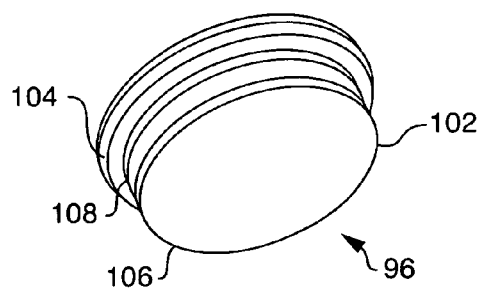
FIG. 28 is another perspective view of the capitellar interface portion.

Referring particularly to FIGS. 26 and 27, articulation portion 96 presents concave articular face 100 and engagement portion 102. Concave articular face 100 may be spheroidal in curvature. Concave articular face 100 is surrounded by rim 104. Engagement portion 102 extends outwardly from articulation portion 98 on the opposite side from concave articular face 100. Engagement portion 102 presents integral snap ring 106 that extends radially outward defining indented circular groove 108.

Figure 22:
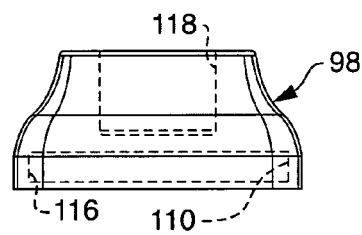
FIG. 22 is a sectional view of the stem interface component of the head of the radial prosthesis with internal structures shown by phantom lines.
Figure 23:
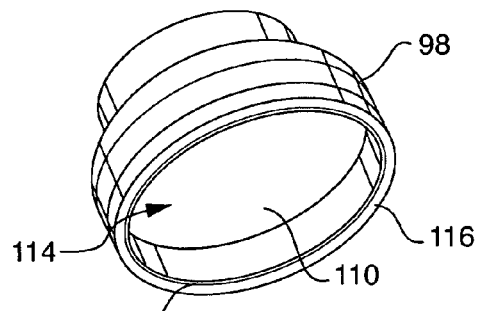
FIG. 23 is a perspective view of the stem interface portion of the head of the radial implant.

Referring particularly to FIGS. 21-24, stem interface portion 98 may be formed from a rigid biocompatible material such as cobalt chrome alloy. Referring particularly to FIGS. 22 and 23, stem interface portion 98 includes articular face cavity 110 which is dimensioned to accept engagement portion 102 and snap ring 106 therein. Articular face cavity 110 presents circular catch ring 112 surrounding the inner edge 114 thereof. Circular catch ring 112 is dimensioned to fit into circular groove 108 while snap ring 106 fits into the perimeter 116 of articular face cavity 110.

Figure 24:
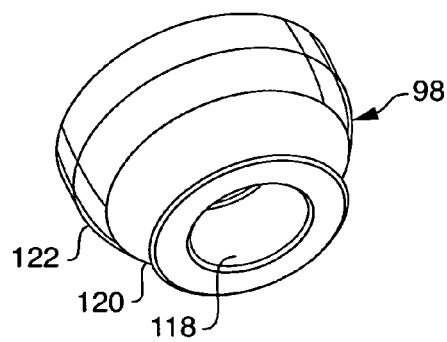
FIG. 24 is a perspective view of the stem interface portion of the head of the radial implant.
Figure 25:
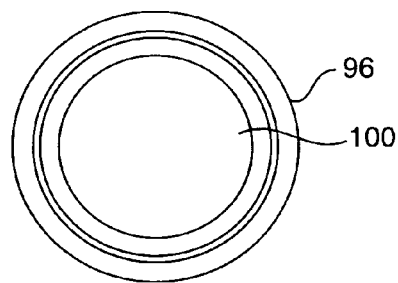
FIG. 25 is a plan view of the capitellar interface portion of the head of the radial implant.

Referring particularly to FIGS. 22 and 24 stem interface portion 98 further presents stem cavity 118. Stem cavity 118 is generally cylindrical in shape and may be formed with a morse taper. Stem interface portion 98 also presents concave portion 120 and convex portion 122. Stem interface portion may be formed of cobalt chrome alloy similar to capitellar prosthesis 42 above. Stem interface portion may be mirror polished over its entire surface with particular attention being paid to concave portion 120 and convex portion 122 which may articulate with soft tissues when implanted within the human body.

In another embodiment of the invention, head 92 may be formed having the same shape and external structure as are articulation portion 96 and stem interface portion 98 together. In this embodiment, the entirety of head 92 may be formed from UHMWPE or another durable self-lubricating material or another polymer or composite.

Referring particularly to FIGS. 7 and 8, stem 94 generally includes bone interface portion 124, collar 126 and extension 128. Bone interface portion 124 has a generally tapering shape with a rounded end 130. Bone interface portion 124 may include a bend 132 occurring approximately halfway between collar 126 and rounded end 130. Bone interface portion 124 may also form a continuous curve. Collar 126 has a diameter larger than both bone interface portion 124 and extension 128. Collar 126 may present an index notch 134 or other marking to indicate the direction of bend 132. Extension 128 is substantially cylindrical in structure and may be formed with a morse taper proportioned to fit into stem cavity 118. Extension 128 and face 136 of collar 126 that make contact with stem interface portion 98 may be mirror polished. The remainder of stem 48 including bone interface portion 124 and the remainder of collar 126 may be roughened to encourage osseointegration such as by application of a commercially pure titanium plasma coating. Stem 48 may take the form of the stem of the radial prosthesis disclosed in U.S. Pat. No. 6,709,459, the contents of which are incorporated herein in their entirety by reference.

Referring particularly to FIGS. 9, 10 and FIGS. 29-36, another embodiment of radial prosthesis 44 is depicted. In this embodiment, radial prosthesis 44 generally includes head 92 and stem 94. Head 92 and stem 94 may be articulated at ball joint 138.

Figure 29:
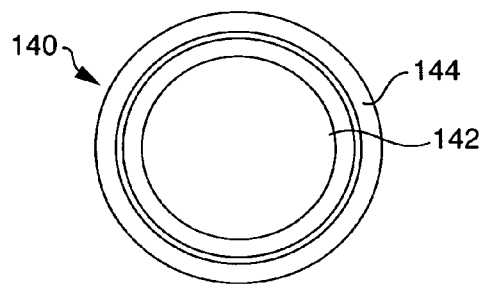
FIG. 29 is a plan view of an alternate embodiment of the radial prosthesis head.
Figure 30:
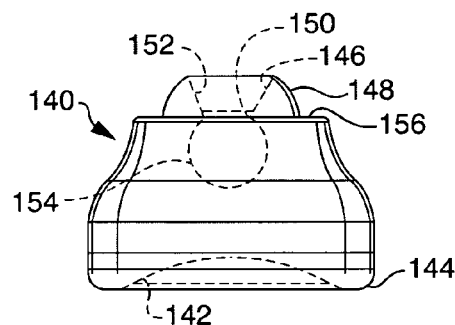
FIG. 30 is a sectional view with phantom lines showing internal structures.
Figure 31:
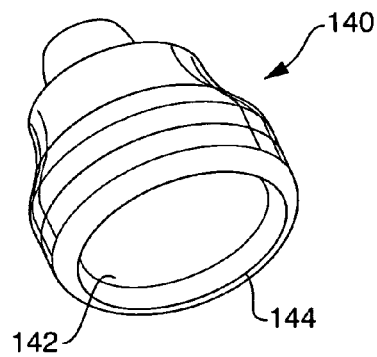
FIG. 31 is a perspective view of the radial component head.
Figure 32:
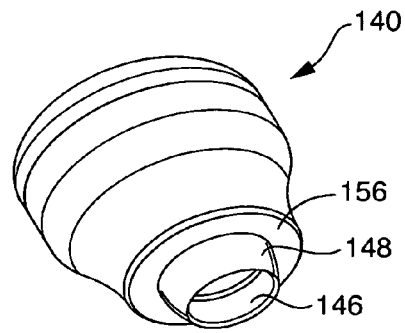
FIG. 32 is another perspective view of the radial component head.
Figure 33:
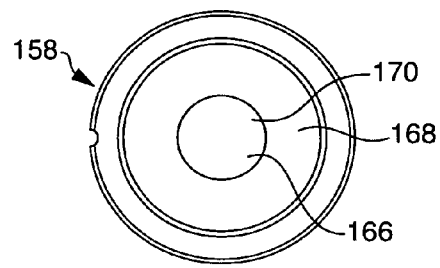
FIG. 33 is a plan view of a stem of an alternate embodiment of the radial head implant.

Referring particularly to FIGS. 29-31, in this embodiment, articular head 140 presents concave articular surface 142 surrounded by a radiused rim 144. Articular head 140 further presents primary joint socket 146 and secondary ball 148. Primary joint socket 146 is a substantially spheroidal cavity within articular head 140 including a narrowed portion 150 and tapered portion 152. Secondary ball 148 includes spheroidal portion 154 and is surrounded by flat 156.

Referring particularly to FIGS. 33-36, in this embodiment stem 94 is articular stem 158. Articular stem generally includes bone interface portion 160 which is substantially similar to bone interface portion 124 of the prior discussed embodiment. Articular stem 158 further presents grooved collar 162 and head interface portion 164.

Figure 34:
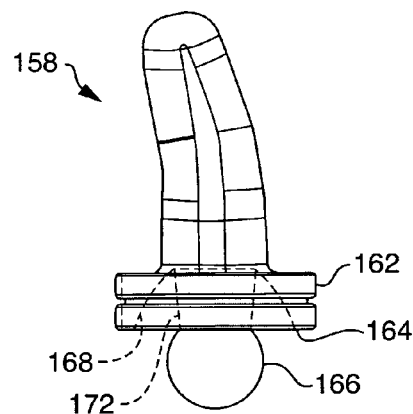
FIG. 34 is an elevational view of the stem showing internal structures in phantom.
Figure 35:
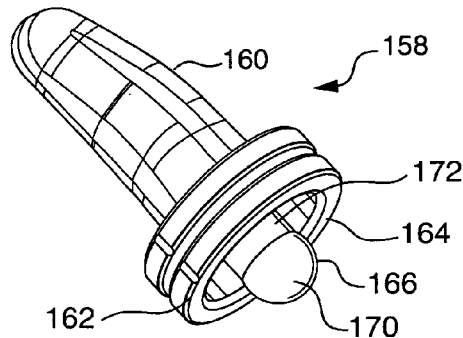
FIG. 35 is a perspective view of an alternate embodiment of the stem of the radial implant.
Figure 36:
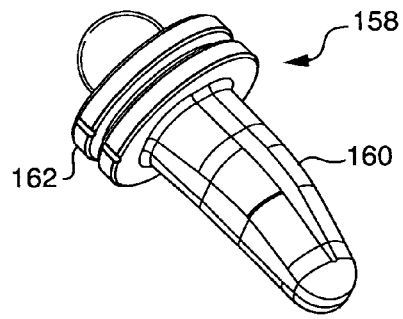
FIG. 36 is another perspective view of an alternate embodiment of the stem of the radial implant.

As seen in FIGS. 34 and 35, articular stem 158 presents primary joint ball 166 and secondary socket 168. Primary joint ball 166 includes spheroidal portion 170 supported by base 172. Secondary socket 168 defines a generally spheroidal cavity surrounding base 172 of primary joint ball 166. Articular stem 158 may be formed from cobalt chrome steel or another biocompatible material such as titanium.

Bone interface portion 160 of articular stem 158 may be roughened to encourage osseointegration such as by application of commercially pure titanium plasma coating. The portions of grooved collar 162 not expected to contact bony tissues and the remainder of head interface portion 164 may be mirror polished to facilitate smooth articulation with soft tissues of the elbow.

In operation, capitellar prosthesis 42 is implanted to replace and/or resurface the capitellum of the humerus. To prepare a space to implant capitellar prosthesis 42 a portion of the capitellum is resected utilizing a resection guide (not shown) corresponding to the location of the first and second facets 62, 64 and a sagittal saw (not shown). Transverse and oblique cuts are made to the deep base of the capitellum and the resected portions are removed. After the capitellum is resected a pilot hole is prepared in the capitellum and drilled into the distal humerus. A broach is then used to enlarge the pilot hole and to shape it appropriately to create a cavity to receive stem 48 of capitellar prosthesis 42. Capitellar prosthesis 42 is intended for cemented implantation. Prior to insertion of capitellar prosthesis 42, stem 48 and bone interface surface 52 are coated with bone cement. If capitellar prosthesis 42 is being utilized for a hemi-arthroplasty of the capitellum without replacement of the head of the radius, then the procedure is complete and the site is closed.

If the radial-capitellar implant 40 is utilized for a complete arthroplasty including replacement of the capitellum with capitellar prosthesis 42 and replacement of the head of the radius with radial prosthesis 44, the following procedure is also performed. Resection of the radial head is performed by making a cut at the radial neck utilizing a resection guide (not shown.) During resection the forearm is pronated and supinated while the cutting guide is used to align the saw blade perpendicular to the axes of rotation of the radius.

The intramedullary canal of the radius is entered using a starter awl in a twisting motion. The intramedullary canal is then broached to the appropriate size and shape to receive stem 94 of radial prosthesis 44. With capitellar prosthesis 42 in place, stem 94 of radial prosthesis 44 is inserted into the broached cavity in the radius and radial prosthesis 44 is assembled by installing head 92 on stem 94. Following assembly of radial prosthesis 44, capitellar prosthesis 42 is articulated with head 92 of radial prosthesis 44. Articular face 50 of capitellar prosthesis 42 articulates with concave articular face 100 of radial prosthesis 44.

If the embodiment of radial prosthesis 44 is utilized that includes articular head 140 connected to articular stem 158 by ball joint 138, articular head 140 also articulates with articular stem 158 about ball joint 138. It is notable that the load born by ball joint 138 is transferred largely at the interface between secondary ball 148 and secondary socket 168 while primary joint ball 166 articulates with primary joint socket 146 and bears a lesser portion of the load. Concave articular face 100 articulates with articular face 50 in both a sliding and a rotational fashion. In addition, ball joint 138 allows conical rotation of articular head 140 relative to articular stem 158 thus adjusting for possible misalignment between articular head 140 and capitellar implant 142.

The above summarizes the technique of implantation of the invention, however a more detailed surgical procedure can be found below.

Surgical Technique

Initial Incision

Place the patient under a general or a regional anesthesia. Make a classic Kocher skin incision identifying the interval between the anconeus muscle and the extensor carpi ulnaris. The incision should extend approximately 6-7 cm. Carry dissection down to the joint capsule. The origin of the anconeus can be released subperiosteally and retracted posteriorly to permit adequate exposure of the capsule.

Capsular Exposure

If the elbow is stable, expose the capsule by elevating a portion of the extensor carpi ulnaris sufficiently to allow identification of the lateral collateral ligament complex. Alternatively, split the extensor carpi ulnaris longitudinally in line with its fibers staying anterior to the attachment of the lateral collateral ligament. Divide the lateral capsule slightly anteriorly to the collateral ligament and the annular ligament and reflect the capsule anteriorly and posteriorly to expose the radial head. A portion of the lateral collateral ligament and anterior capsule can be reflected off the lateral epicondyle and anterior humerus to expose the capitellum. The lateral ulno-humeral ligament should not be disturbed. If the ligament has been disrupted, then proceed through the site of disruption to expose the radiohumeral joint. Retract the common extensor tendon and elbow joint capsule as needed to maximize exposure.

Capitellar Resection Guide

Place the capitellar resection guide (not shown) over the capitellum. Perform transverse and oblique cuts to the deep base of the capitellum. Using a rongeur, remove the capitellar head and trim remaining fragments, as needed.

Capitellar Trial and Drill Guide

Place a capitellar trial (not shown) against the resected humerus. Insert K-wires through holes in the trial and into the distal humerus to firmly seat the trial component. Using an appropriately sized drill, drill a broach pilot hole into the distal humerus. If using the capitellar implant alone as a hemi-arthroplasty of the capitellum, radial head resection is not necessary, therefore proceed to the step of Intramedullary Preparation, Distal Humerus below.

Radial Head Resection Guide

Resect the radial neck utilizing a resection guide (not shown.) Resection of the radius utilizing a resection guide is disclosed in U.S. Pat. No. 6,709,459.

During the resection, the forearm is pronated and supinated while the cutting guide is used to align the sawblade perpendicular to the axis of rotation defined by the resection guide. The extent of resection of the radius should be minimized. For example, the distal extent of resection may be the minimal amount that is consistent with the restoration of function as dictated by a fracture line in the radius or a previous radial head resection. In addition, radial length should be restored using a lamina spreader to apply axial traction if there is a positive ulna variance.

Intramedullary Preparation, Proximal Radius

If the elbow is unstable, varus stress and rotation of the forearm into supination allows improved access to the medullary canal. If the elbow is stable but the exposure is not adequate to access the medullary canal, careful reflection of the origin of the collateral ligament from the lateral epicondyle may be necessary to permit subluxation to access the medullary canal. Enter the canal with a starter awl using a twisting motion. Broach the canal taking care to identify the proper axial orientation. The forearm should be in mid-rotation with the tuberosity directed medially. This position is favorable for broaching and implantation as the curve of the broach/implant points lateral or away from the radial tuberosity. Serial sized broaches are used until the broach fits snugly in the canal to an appropriate depth.

Trial Reduction, Proximal Radius

A trial stem is inserted into the broached cavity and a trial radial head is placed on the trial stem. Assure that the stem's collar is flush with the resected head of the radius. Tracking, both in flexion and extension and forearm rotation should be carefully assessed. Misalignment of the radial osteotomy will cause abnormal tracking during flexion-extension and/or forearm pronation and supination. Remove the radial head and stem trials if tracking and alignment is satisfactory.

Intramedullary Preparation, Distal Humerus

Remove the capitellar trial and K-wires to allow access to the broach pilot hole. Insert broach into the pilot hole and impact. Care should be taken to maintain proper alignment with the drilled pilot hole. Continue broaching the distal humerus until the broach fits snugly in the canal to an appropriate depth.

Implanting the Final Components

Once acceptable alignment has been determined, a permanent prosthesis can be inserted. Distraction of the proximal radius may be necessary to allow sufficient access for capitellar prosthesis 42 insertion. Insert the stem 48 into the canal and tap into place using an impactor (not shown). Polymethyl methacrylate (PMMA) bone cement is recommended for the capitellar component. If using the capitellar prosthesis 42 as a hemi-arthroplasty of the capitellum, proceed to the step of Closure below.

Insert the radial stem 94 of radial prosthesis 44 into the intramedullary canal of the proximal radius and tap it into place with an impactor. Bone cement is recommended unless a secure fixation is present at the time of the insertion of the trial stem (i.e. stem cannot be easily extracted from the medullary canal). Next, place head 92 over extension 128 using longitudinal distraction and/or varus stress to distract the radio capitellar interface sufficiently to permit head 92 to be placed on extension 128. Once inserted, secure head 92 using an impactor or an assembly tool. Reduce the elbow and again test the range of motion in flexion/extension and pronation/supination.

Closure

Close the incision. The forearm is placed in full or partial rotation before sutures are tied. The elbow is splinted at 90 degrees flexion and in neutral to full pronation.

Aftercare

Passive flexion and extension is permitted on the second day assuming the elbow is considered stable. The goal of radial head replacement and soft tissue repair is to achieve elbow stability.

Both flexion/extension and pronation/supination arcs are allowed without restriction. Active motion can begin by day five. Long term aftercare requires monitoring as with any prosthetic replacement.

The present invention may be embodied in other specific forms without departing from the central attributes thereof, therefore, the illustrated embodiment should be considered in all respects as illustrative and not restrictive, reference being made to the appended claims rather than the foregoing description to indicate the scope of the invention.

What is claimed is:

1. An implantable joint prosthesis for implantation at the radiocapitellar joint, the joint prosthesis comprising:
   a capitellar prosthesis configured to replace a capitellum while leaving an adjacent trochlea substantially intact, the capitellar prosthesis comprising:
      a body having a smooth convex articular surface having a lateral flat adapted to allow for excursion of the radial nerve over the articular surface, and a bone interface surface on a side of the body opposite to the convex articular surface, the bone interface surface having a first facet and a second facet positioned inferior to the first facet, the first facet being oriented relative to the second facet at an obtuse angle on the side of the body opposite the convex articular surface; and
      a first stem extending outwardly away from the bone interface surface, the stem including a lateral side, a medial side, a superior side and an inferior side, the medial side having a bend along a portion of the medial side and the lateral side is angled approximately 5 degrees relative to a centerline of the stem.

2. The joint prosthesis as claimed in claim 1, wherein the convex articular surface is substantially a partial spheroid.

3. The joint prosthesis as claimed in claim 1, wherein the convex articular surface extends along an arc of about one hundred seventy to about one hundred ninety degrees in a first direction and along an arc of about eighty to about one hundred degrees in a second direction, the second direction being substantially normal to the first direction.

4. The joint prosthesis as claimed in claim 1, wherein the first stem is treated to promote osseointegration.

5. The joint prosthesis as claimed in claim 1, wherein the first stem has a substantially quadrilateral cross section.

6. The joint prosthesis as claimed in claim 1, wherein the first stem is substantially tapered along its length.

7. The joint prosthesis as claimed in claim 1, wherein the first stem extends outwardly from the bone interface surface at a junction between the first facet and the second facet.

8. The joint prosthesis as claimed in claim 1 further comprising:
   a radial head prosthesis, the radial head prosthesis comprising a second stem and a head, the head having a concave articular surface.

9. The joint prosthesis as claimed in claim 8, wherein the concave articular surface is formed of UHMWPE.

10. The joint prosthesis as claimed in claim 8, wherein the concave articular surface is formed of a polymeric substance.

11. The joint prosthesis as claimed in claim 8, wherein the convex articular surface of the capitellar prosthesis is substantially a partial spheroid.

12. The joint prosthesis as claimed in claim 8, wherein the convex articular surface of the capitellar prosthesis has a lateral flat adapted to allow for excursion of the radial nerve over the articular surface.

13. The joint prosthesis as claimed in claim 8, wherein the convex articular surface extends along an arc of about one hundred seventy to about one hundred ninety degrees in a first direction and along an arc of about eighty to about one hundred degrees in a second direction, the second direction being substantially normal to the first direction.

14. The joint prosthesis as claimed in claim 8, wherein at least a portion of the capitellar prosthesis is treated to promote osseointegration.

15. The joint prosthesis as claimed in claim 8, wherein the first stem has a substantially quadrilateral cross section.

16. The joint prosthesis as claimed in claim 8, wherein the first stem is substantially tapered along its length.

17. The joint prosthesis as claimed in claim 8, wherein the first stem extends outwardly from the bone interface surface at a junction between the first facet and the second facet.

18. The joint prosthesis as claimed in claim 1 further comprising:
   a radial head prosthesis, the radial head prosthesis comprising a second stem and a head, the head having a concave articular surface, the head being formed entirely from UHMWPE.

19. The joint prosthesis as claimed in claim 1 further comprising:
   a radial prosthesis, the radial prosthesis comprising a second stem and a head, the head being articulated to the second stem by a ball joint.

20. The joint prosthesis as claimed in claim 19, wherein the ball joint comprises a primary ball articulable into a primary joint socket and a secondary ball articulable into a secondary joint socket.

21. The joint prosthesis as claimed in claim 20, wherein the primary ball is supported by the second stem, the primary socket is defined by the head, the secondary ball is supported by the head and the secondary socket is defined by the second stem.

22. The joint prosthesis as claimed in claim 20, wherein the primary ball, the primary socket, the secondary ball and the secondary socket share a substantially commonly located center.

23. The joint prosthesis as claimed in claim 1, wherein the first stem further comprises at least one of the lateral side, inferior side and superior side as planar from proximate an end of the first stem to proximate the bone interface.

24. The joint prosthesis as claimed in claim 23, wherein a portion of the medial side proximal to the bend is angled approximately 95 degrees relative to the first facet.

25. The joint prosthesis as claimed in claim 23, wherein a portion of the medial side distal to the bend is angled approximately 3 degrees relative to a centerline of the stem.

26. The joint prosthesis as claimed in claim 23, wherein each of the lateral side, inferior side and superior side is planar.

27. The implantable joint prosthesis of claim 26, wherein a cross-section of the end of the first stem is substantially quadrilateral.

28. The joint prosthesis as claimed in claim 1, wherein the convex articular surface of the capitellar prosthesis includes a first lateral surface and a second lateral surface.

29. The joint prosthesis as claimed in claim 28, wherein the first lateral surface is planar and the second lateral surface includes a planer portion and a curved portion.

30. The joint prosthesis as claimed in claim 1, wherein the bend is on a medial side of the first stem relative to the radiocapitellar joint when the joint prosthesis is implanted.

31. The joint prosthesis as claimed in claim 1, wherein the bend is formed between a proximal surface and a distal surface, the proximal surface forming an angle with the first facet of approximately 95 degrees.

* * * * *